US009498175B2

(12) United States Patent
Stein et al.

(10) Patent No.: US 9,498,175 B2
(45) Date of Patent: *Nov. 22, 2016

(54) SYSTEM AND METHOD FOR LOW DOSE TOMOSYNTHESIS

(71) Applicant: Hologic, Inc., Bedford, MA (US)

(72) Inventors: Jay Stein, Boston, MA (US); Andrew P. Smith, Lexington, MA (US); Zhenxue Jing, Chadds Ford, PA (US); Loren Niklason, N Tetonia, ID (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/057,061

(22) Filed: Oct. 18, 2013

(65) Prior Publication Data

US 2014/0044230 A1 Feb. 13, 2014
US 2016/0270742 A9 Sep. 22, 2016

Related U.S. Application Data

(63) Continuation of application No. 12/397,013, filed on Mar. 9, 2009, now Pat. No. 8,565,372, which is a continuation-in-part of application No. 11/791,601, filed as application No. PCT/US05/42613 on Nov. 26, 2003, now Pat. No. 7,869,563, which is a continuation-in-part of application No. 10/723,486, filed on Nov. 26, 2003, now Pat. No. 7,831,296.

(51) Int. Cl.
*A61B 6/00* (2006.01)
*G01N 23/04* (2006.01)
*A61B 6/02* (2006.01)

(52) U.S. Cl.
CPC ............. *A61B 6/4417* (2013.01); *A61B 6/405* (2013.01); *A61B 6/502* (2013.01); *A61B 6/5235* (2013.01); *G01N 23/046* (2013.01); *A61B 6/025* (2013.01); *A61B 6/5247* (2013.01); *A61B 6/542* (2013.01)

(58) Field of Classification Search
CPC .......... A61B 6/00; A61B 6/02; A61B 6/025; A61B 6/40; A61B 6/405; A61B 6/44; A61B 6/4411; A61B 6/4417; A61B 6/48; A61B 6/50; A61B 6/502; G01N 23/00; G01N 23/02; G01N 23/04; G01N 23/046
USPC .......... 378/21–26, 37, 51, 53, 62, 91, 96–98, 378/98.8, 108–112, 193, 197, 204, 210; 382/128, 131, 132, 276, 282, 325
See application file for complete search history.

(56) References Cited

U.S. PATENT DOCUMENTS 3,502,878 A 3/1970 Stewart
3,863,073 A 1/1975 Wagner
(Continued)

FOREIGN PATENT DOCUMENTS

DE 102004051401 5/2006
EP 0775467 5/1997
(Continued)

OTHER PUBLICATIONS

Wheeler, F. W. et al., "Micro-Calcification Detection in Digital Tomosynthesis Mammography", Proceedings of SPIE, Dec. 11, 2001, to Dec. 15, 2001, vol. 6144, Feb. 13, 2006.
(Continued)

*Primary Examiner* — Anastasia Midkiff

(57) ABSTRACT

A breast imaging system leverages the combined strengths of two-dimensional and three-dimensional imaging to provide a breast cancer screening with improved sensitivity, specificity and patient dosing. A tomosynthesis system supports the acquisition of three-dimensional images at a dosage lower than that used to acquire a two-dimensional image. The low-dose three-dimensional image may be used for mass detection, while the two-dimensional image may be used for calcification detection. Obtaining tomosynthesis data at low dose provides a number of advantages in addition to mass detection including the reduction in scan time and wear and tear on the x-ray tube. Such an arrangement provides a breast cancer screening system with high sensitivity and specificity and reduced patient dosing.

20 Claims, 7 Drawing Sheets

(56) References Cited

U.S. PATENT DOCUMENTS

| | | | |
|---|---|---|---|
| 3,971,950 A | 7/1976 | Evans et al. | |
| 4,160,906 A | 7/1979 | Daniels et al. | |
| 4,310,766 A | 1/1982 | Finkenzeller et al. | |
| 4,496,557 A | 1/1985 | Malen et al. | |
| 4,513,433 A | 4/1985 | Weiss et al. | |
| 4,559,641 A | 12/1985 | Caugant et al. | |
| 4,662,379 A | 5/1987 | Macovski | |
| 4,706,269 A | 11/1987 | Reina et al. | |
| 4,744,099 A | 5/1988 | Huettenrauch et al. | |
| 4,773,086 A | 9/1988 | Fujita et al. | |
| 4,773,087 A | 9/1988 | Plewes | |
| 4,819,258 A | 4/1989 | Kleinman et al. | |
| 4,821,727 A | 4/1989 | Levene et al. | |
| 4,969,174 A | 11/1990 | Scheid et al. | |
| 4,989,227 A | 1/1991 | Tirelli et al. | |
| 5,018,176 A | 5/1991 | Romeas et al. | |
| RE33,634 E | 7/1991 | Yanaki | |
| 5,029,193 A | 7/1991 | Saffer | |
| 5,051,904 A | 9/1991 | Griffith | |
| 5,078,142 A | 1/1992 | Siczek et al. | |
| 5,163,075 A | 11/1992 | Lubinsky et al. | |
| 5,164,976 A | 11/1992 | Scheid et al. | |
| 5,199,056 A | 3/1993 | Darrah | |
| 5,212,637 A | 5/1993 | Saxena | |
| 5,240,011 A | 8/1993 | Assa | |
| 5,289,520 A | 2/1994 | Pellegrino et al. | |
| 5,291,539 A | 3/1994 | Thumann et al. | |
| 5,359,637 A | 10/1994 | Webber | |
| 5,365,562 A | 11/1994 | Toker | |
| 5,415,169 A | 5/1995 | Siczek et al. | |
| 5,426,685 A | 6/1995 | Pellegrino et al. | |
| 5,452,367 A | 9/1995 | Bick et al. | |
| 5,506,877 A | 4/1996 | Niklason et al. | |
| 5,526,394 A | 6/1996 | Siczek et al. | |
| 5,539,797 A | 7/1996 | Heidsieck et al. | |
| 5,553,111 A | 9/1996 | Moore et al. | |
| 5,592,562 A | 1/1997 | Rooks | |
| 5,594,769 A | 1/1997 | Pellegrino et al. | |
| 5,596,200 A | 1/1997 | Sharma et al. | |
| 5,598,454 A | 1/1997 | Franetzke et al. | |
| 5,609,152 A | 3/1997 | Pellegrino et al. | |
| 5,627,869 A | 5/1997 | Andrew et al. | |
| 5,657,362 A | 8/1997 | Giger et al. | |
| 5,668,844 A | 9/1997 | Webber | |
| 5,668,889 A | 9/1997 | Hara | |
| 5,706,327 A | 1/1998 | Adamkowski et al. | |
| 5,719,952 A | 2/1998 | Rooks | |
| 5,735,264 A | 4/1998 | Siczek et al. | |
| 5,769,086 A | 6/1998 | Ritchart et al. | |
| 5,803,912 A | 9/1998 | Siczek et al. | |
| 5,818,898 A | 10/1998 | Tsukamoto et al. | |
| 5,828,722 A | 10/1998 | Ploetz et al. | |
| 5,844,965 A | 12/1998 | Galkin | |
| 5,872,828 A | 2/1999 | Niklason et al. | |
| 5,878,104 A | 3/1999 | Ploetz | |
| 5,896,437 A | 4/1999 | Ploetz | |
| 5,941,832 A | 8/1999 | Tumey et al. | |
| 5,970,118 A | 10/1999 | Sokolov | |
| 5,986,662 A | 11/1999 | Argiro et al. | |
| 5,999,836 A | 12/1999 | Nelson et al. | |
| 6,005,907 A | 12/1999 | Ploetz | |
| 6,022,325 A | 2/2000 | Siczek et al. | |
| 6,075,879 A | 6/2000 | Roehrig et al. | |
| 6,091,841 A | 7/2000 | Rogers et al. | |
| 6,137,527 A | 10/2000 | Abdel-Malek et al. | |
| 6,141,398 A | 10/2000 | He et al. | |
| 6,149,301 A | 11/2000 | Kautzer et al. | |
| 6,175,117 B1 | 1/2001 | Komardin et al. | |
| 6,196,715 B1 | 3/2001 | Nambu et al. | |
| 6,216,540 B1 | 4/2001 | Nelson et al. | |
| 6,219,059 B1 | 4/2001 | Argiro | |
| 6,233,473 B1 | 5/2001 | Shepherd et al. | |
| 6,243,441 B1 | 6/2001 | Zur | |
| 6,256,370 B1 | 7/2001 | Yavuz | |
| 6,272,207 B1 | 8/2001 | Tang | |
| 6,289,235 B1 | 9/2001 | Webber et al. | |
| 6,292,530 B1 | 9/2001 | Yavus et al. | |
| 6,327,336 B1 | 12/2001 | Gingold et al. | |
| 6,341,156 B1 | 1/2002 | Baetz et al. | |
| 6,375,352 B1 | 4/2002 | Hewes et al. | |
| 6,411,836 B1 | 6/2002 | Patel et al. | |
| 6,415,015 B2 | 7/2002 | Nicolas et al. | |
| 6,442,288 B1 | 8/2002 | Haerer et al. | |
| 6,459,925 B1 | 10/2002 | Nields et al. | |
| 6,480,565 B1 | 11/2002 | Ning | |
| 6,490,476 B1 | 12/2002 | Townsend et al. | |
| 6,501,819 B2 | 12/2002 | Unger et al. | |
| 6,556,655 B1 | 4/2003 | Chichereau et al. | |
| 6,574,304 B1 | 6/2003 | Hsieh et al. | |
| 6,574,629 B1 | 6/2003 | Cooke, Jr. | |
| 6,597,762 B1 | 7/2003 | Ferrant et al. | |
| 6,611,575 B1 | 8/2003 | Alyassin et al. | |
| 6,620,111 B2 | 9/2003 | Stephens et al. | |
| 6,626,849 B2 | 9/2003 | Huitema et al. | |
| 6,633,674 B1 | 10/2003 | Barnes et al. | |
| 6,638,235 B2 | 10/2003 | Miller et al. | |
| 6,647,092 B2 | 11/2003 | Eberhard et al. | |
| 6,744,848 B2 | 6/2004 | Stanton et al. | |
| 6,748,044 B2 | 6/2004 | Sabol et al. | |
| 6,751,285 B2 | 6/2004 | Eberhard et al. | |
| 6,758,824 B1 | 7/2004 | Miller et al. | |
| 6,813,334 B2 | 11/2004 | Koppe et al. | |
| 6,882,700 B2 | 4/2005 | Wang et al. | |
| 6,885,724 B2 | 4/2005 | Li et al. | |
| 6,909,790 B2 | 6/2005 | Chiu et al. | |
| 6,909,792 B1 | 6/2005 | Carrott et al. | |
| 6,912,319 B1 | 6/2005 | Barnes et al. | |
| 6,940,943 B2 | 9/2005 | Claus et al. | |
| 6,957,099 B1 | 10/2005 | Arnone et al. | |
| 6,970,531 B2 | 11/2005 | Eberhard et al. | |
| 6,978,040 B2 | 12/2005 | Berestov | |
| 6,987,831 B2 | 1/2006 | Ning | |
| 6,999,554 B2 | 2/2006 | Mertelmeier | |
| 7,110,490 B2 | 9/2006 | Eberhard et al. | |
| 7,110,502 B2 | 9/2006 | Tsuji | |
| 7,123,684 B2 | 10/2006 | Jing et al. | |
| 7,127,091 B2 | 10/2006 | Op De Beek et al. | |
| 7,142,633 B2 | 11/2006 | Eberhard et al. | |
| 7,245,694 B2 | 7/2007 | Jing et al. | |
| 7,302,031 B2 | 11/2007 | Hjarn et al. | |
| 7,315,607 B2 | 1/2008 | Ramsauer | |
| 7,319,735 B2 | 1/2008 | Defreitas et al. | |
| 7,323,692 B2 | 1/2008 | Rowlands et al. | |
| 7,430,272 B2 | 9/2008 | Jing et al. | |
| 7,443,949 B2 | 10/2008 | Defreitas et al. | |
| 7,577,282 B2 | 8/2009 | Gkanatsios et al. | |
| 7,583,786 B2 | 9/2009 | Jing et al. | |
| 7,609,806 B2 | 10/2009 | Defreitas et al. | |
| 7,616,801 B2 | 11/2009 | Gkanatsios et al. | |
| 7,630,531 B2 | 12/2009 | Chui | |
| 7,630,533 B2 | 12/2009 | Ruth et al. | |
| 7,688,940 B2 | 3/2010 | Defreitas et al. | |
| 7,697,660 B2 | 4/2010 | Ning | |
| 7,702,142 B2 | 4/2010 | Ren et al. | |
| 7,760,853 B2 | 7/2010 | Jing et al. | |
| 7,760,924 B2 | 7/2010 | Ruth et al. | |
| 7,792,245 B2 | 9/2010 | Hitzke et al. | |
| 7,831,296 B2 * | 11/2010 | DeFreitas et al. | 600/427 |
| 7,869,563 B2 * | 1/2011 | Defreitas et al. | 378/37 |
| 7,881,428 B2 | 2/2011 | Jing et al. | |
| 7,894,646 B2 | 2/2011 | Shirahata et al. | |
| 7,916,915 B2 | 3/2011 | Gkanatsios et al. | |
| 7,949,091 B2 | 5/2011 | Jing et al. | |
| 7,986,765 B2 | 7/2011 | Defreitas et al. | |
| 7,991,106 B2 | 8/2011 | Ren et al. | |
| 8,131,049 B2 | 3/2012 | Ruth et al. | |
| 8,155,421 B2 | 4/2012 | Ren et al. | |
| 8,170,320 B2 | 5/2012 | Smith et al. | |
| 8,175,219 B2 * | 5/2012 | Defreitas et al. | 378/37 |
| 8,285,020 B2 | 10/2012 | Gkanatsios et al. | |
| 8,416,915 B2 | 4/2013 | Jing et al. | |
| 8,452,379 B2 | 5/2013 | DeFreitas et al. | |
| 8,559,595 B2 | 10/2013 | DeFreitas et al. | |
| 8,565,372 B2 * | 10/2013 | Stein et al. | 378/37 |

(56) References Cited

U.S. PATENT DOCUMENTS

| | | | |
|---|---|---|---|
| 8,565,374 B2* | 10/2013 | Defreitas et al. | 378/37 |
| 8,571,289 B2 | 10/2013 | Ruth et al. | |
| 8,712,127 B2 | 4/2014 | Ren et al. | |
| 8,831,171 B2 | 9/2014 | Jing et al. | |
| 9,042,612 B2 | 5/2015 | Gkanatsios et al. | |
| 2001/0038681 A1 | 11/2001 | Stanton et al. | |
| 2002/0012450 A1 | 1/2002 | Tsujii | |
| 2002/0048343 A1 | 4/2002 | Launay et al. | |
| 2002/0050986 A1 | 5/2002 | Inoue et al. | |
| 2002/0070970 A1 | 6/2002 | Wood et al. | |
| 2002/0075997 A1 | 6/2002 | Unger et al. | |
| 2003/0007598 A1 | 1/2003 | Wang et al. | |
| 2003/0018272 A1 | 1/2003 | Treado et al. | |
| 2003/0026386 A1 | 2/2003 | Tang et al. | |
| 2003/0072417 A1 | 4/2003 | Kaufhold et al. | |
| 2003/0073895 A1 | 4/2003 | Nields et al. | |
| 2003/0095624 A1 | 5/2003 | Eberhard et al. | |
| 2003/0097055 A1 | 5/2003 | Yanof et al. | |
| 2003/0169847 A1 | 9/2003 | Karellas et al. | |
| 2003/0194050 A1 | 10/2003 | Eberhard et al. | |
| 2003/0194051 A1 | 10/2003 | Wang et al. | |
| 2003/0194121 A1 | 10/2003 | Eberhard et al. | |
| 2003/0210254 A1 | 11/2003 | Doan et al. | |
| 2003/0212327 A1 | 11/2003 | Wang et al. | |
| 2003/0215120 A1 | 11/2003 | Uppaluri et al. | |
| 2004/0008809 A1 | 1/2004 | Webber | |
| 2004/0066882 A1 | 4/2004 | Eberhard et al. | |
| 2004/0066884 A1 | 4/2004 | Hermann Claus et al. | |
| 2004/0066904 A1 | 4/2004 | Eberhard et al. | |
| 2004/0070582 A1 | 4/2004 | Smith et al. | |
| 2004/0094167 A1 | 5/2004 | Brady et al. | |
| 2004/0101095 A1 | 5/2004 | Jing et al. | |
| 2004/0109529 A1* | 6/2004 | Eberhard et al. | 378/23 |
| 2004/0146221 A1 | 7/2004 | Siegel et al. | |
| 2004/0171986 A1 | 9/2004 | Tremaglio, Jr. et al. | |
| 2004/0267157 A1 | 12/2004 | Miller et al. | |
| 2005/0049521 A1 | 3/2005 | Miller et al. | |
| 2005/0063509 A1 | 3/2005 | DeFreitas et al. | |
| 2005/0078797 A1 | 4/2005 | Danielsson et al. | |
| 2005/0105679 A1 | 5/2005 | Wu et al. | |
| 2005/0113681 A1 | 5/2005 | DeFreitas et al. | |
| 2005/0113715 A1 | 5/2005 | Schwindt et al. | |
| 2005/0129172 A1* | 6/2005 | Mertelmeier | 378/37 |
| 2005/0135555 A1 | 6/2005 | Claus et al. | |
| 2005/0135664 A1 | 6/2005 | Kaufhold et al. | |
| 2005/0226375 A1 | 10/2005 | Eberhard et al. | |
| 2006/0030784 A1 | 2/2006 | Miller et al. | |
| 2006/0074288 A1 | 4/2006 | Kelly | |
| 2006/0098855 A1 | 5/2006 | Gkanatsios et al. | |
| 2006/0129062 A1 | 6/2006 | Nicoson et al. | |
| 2006/0155209 A1 | 7/2006 | Miller et al. | |
| 2006/0269041 A1 | 11/2006 | Mertelmeier | |
| 2006/0291618 A1 | 12/2006 | Eberhard et al. | |
| 2007/0030949 A1 | 2/2007 | Jing et al. | |
| 2007/0036265 A1 | 2/2007 | Jing et al. | |
| 2007/0076844 A1 | 4/2007 | Defreitas et al. | |
| 2007/0078335 A1 | 4/2007 | Horn | |
| 2007/0140419 A1* | 6/2007 | Souchay | 378/37 |
| 2007/0223651 A1 | 9/2007 | Wagenaar et al. | |
| 2007/0225600 A1 | 9/2007 | Weibrecht et al. | |
| 2007/0242800 A1 | 10/2007 | Jing et al. | |
| 2008/0019581 A1 | 1/2008 | Gkanatsios et al. | |
| 2008/0045833 A1 | 2/2008 | Defreitas et al. | |
| 2008/0101537 A1 | 5/2008 | Sendai | |
| 2008/0112534 A1 | 5/2008 | Defreitas | |
| 2008/0130979 A1 | 6/2008 | Ren | |
| 2008/0212861 A1 | 9/2008 | Durgan et al. | |
| 2009/0003519 A1 | 1/2009 | Defreitas et al. | |
| 2009/0010384 A1 | 1/2009 | Jing et al. | |
| 2009/0080594 A1 | 3/2009 | Brooks et al. | |
| 2009/0080602 A1 | 3/2009 | Brooks et al. | |
| 2009/0135997 A1 | 5/2009 | Defreitas et al. | |
| 2009/0141859 A1 | 6/2009 | Gkanatsios et al. | |
| 2009/0213987 A1 | 8/2009 | Stein et al. | |
| 2009/0238424 A1 | 9/2009 | Arakita et al. | |
| 2009/0268865 A1 | 10/2009 | Ren et al. | |
| 2009/0296882 A1 | 12/2009 | Gkanatsios | |
| 2009/0304147 A1 | 12/2009 | Jing et al. | |
| 2010/0034450 A1 | 2/2010 | Mertelmeier | |
| 2010/0054400 A1 | 3/2010 | Ren | |
| 2010/0086188 A1 | 4/2010 | Ruth | |
| 2010/0150306 A1 | 6/2010 | Defreitas et al. | |
| 2010/0195882 A1 | 8/2010 | Ren | |
| 2010/0226475 A1 | 9/2010 | Smith | |
| 2010/0290585 A1 | 11/2010 | Eliasson | |
| 2011/0069809 A1 | 3/2011 | Defreitas et al. | |
| 2011/0178389 A1 | 7/2011 | Kumar et al. | |
| 2011/0234630 A1 | 9/2011 | Batman et al. | |
| 2013/0028374 A1 | 1/2013 | Gkanatsios et al. | |
| 2014/0044231 A1 | 2/2014 | Defreitas et al. | |
| 2014/0086471 A1 | 3/2014 | Ruth et al. | |
| 2014/0098935 A1 | 4/2014 | Defreitas et al. | |
| 2014/0232752 A1 | 8/2014 | Ren et al. | |
| 2014/0376690 A1 | 12/2014 | Jing et al. | |
| 2015/0049859 A1 | 2/2015 | DeFreitas et al. | |
| 2015/0160848 A1 | 6/2015 | Gkanatsios et al. | |
| 2015/0310611 A1 | 10/2015 | Gkanatsios et al. | |

FOREIGN PATENT DOCUMENTS

| | | | |
|---|---|---|---|
| EP | 0982001 | 3/2000 | |
| EP | 1428473 | 6/2004 | |
| EP | 1759637 | 3/2007 | |
| EP | 1569556 | 4/2012 | |
| EP | 2602743 | 11/2014 | |
| JP | 2001346786 | 12/2001 | |
| JP | 2006-231054 | 9/2006 | |
| JP | 2007-50264 | 3/2007 | |
| JP | 2007-521911 | 8/2007 | |
| JP | 2008-67933 | 3/2008 | |
| WO | WO 90/05485 | 5/1990 | |
| WO | WO 90/05495 | 5/1990 | |
| WO | WO 98/16903 | 4/1998 | |
| WO | WO 00/51484 | 9/2000 | |
| WO | WO 03/020114 | 3/2003 | |
| WO | WO 03/057564 | 7/2003 | |
| WO | WO 2004/043535 | 5/2004 | |
| WO | WO 2005/051197 | 6/2005 | |
| WO | WO 2005/110230 | 11/2005 | |
| WO | WO 2005/112767 | 12/2005 | |
| WO | WO 2006/055830 | 5/2006 | |
| WO | WO 2006058160 A2* | 6/2006 | G06K 9/00 |

OTHER PUBLICATIONS

Wu Tao, et al., "Tomographic Mammography Using a Limited Number of Low-Dose Cone-Beam Projection Images", Medical Physics, vol. 30, No. 3, Mar. 1, 2003, pp. 365-380.

"Essentials for life: Senographe Essential Full-Field Digital Mammography system", GE Health-care Brochure, MM-0132-05.06-EN-US, 2006, 12 pgs.

"Filtered Back Projection," (Nygren) published May 8, 2007; URL:http://web.archive.org/web/19991010131715/http://www.owlnet.rice.edu/-.about.elec539/Projects97/cult/node2.html., 2 pgs.

"Lorad Selenia" Document B-Bi-SEO US/Intl (May 2006) copyright Hologic 2006, 12 pgs.

Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.

Chan, Heang-Ping et al., "ROC study of the effect of stereoscopic imaging on assessment of breast lesions", Medical Physics, vol. 32, No. 4, Apr. 2005, 7 pgs.

Cole, Elodia, et al., "The Effects of Gray Scale Image Processing on Digital Mammography Interpretation Performance", Academic Radiology, vol. 12, No. 5, pp. 585-595, May 2005.

Digital Clinical Reports, Tomosynthesis, GE Brochure 98-5493, Nov. 1998, 8 pgs.

Dobbins, James T., "Digital x-ray tomosynthesis: current state of the art and clinical potential," Physics in Medicine and Biology, Taylor and Francis LTD, London GB, vol. 48, No. 19, Oct. 7, 2003, 42 pages.

(56) References Cited

OTHER PUBLICATIONS

Federica Pediconi et al., "Color-coded automated signal intensity-curve for detection and characterization of breast lesions: Preliminary evaluation of a new software for MR-based breast imaging", International Congress Series 1281 (2005) 1081-1086.

Grant, David G., "Tomosynthesis: a three-dimensional imaging technique", IEEE Trans. Biomed. Engineering, vol. BME-19, #1, Jan. 1972, pp. 20-28.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Mammographic Accreditation Phantom, http://www.cirsinc.com/pdfs/015cp.pdf. (2006), 2 pgs.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.

Smith, A., "Fundamentals of Breast Tomosynthesis", White Paper, Hologic Inc., WP-00007, Jun. 2008, 8 pgs.

Acrin website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosnythesis", obtained online on Dec. 8, 2015, 5 pgs.

American College of Radiology website, located at http://www.acr.org/FAQs/DBT-FAQ, "Digital Breast Tomosynthesis FAQ for Insurers", obtained online on Dec. 8, 2015, 2 pages.

Niklason, Loren T. et al., "Digital Tomosynthesis in Breast Imaging", Radiology, Nov. 1997, vol. 205, No. 2, pp. 399-406.

Pisano, Etta D., "Digital Mammography", Radiology, vol. 234, No. 2, Feb. 2005, pp. 353-362.

Smith, Andrew, PhD, "Full Field Breast Tomosynthesis", Hologic White Paper, Oct. 2004, 6 pgs.

\* cited by examiner

SYSTEM AND METHOD FOR LOW DOSE TOMOSYNTHESIS

RELATED APPLICATIONS

This application is a continuation application and claims priority under 35 U.S.C. §120 to U.S. patent application Ser. No. 12/397,013 filed Mar. 3, 2009, now U.S. Pat. No. 8,565,372; which is a continuation-in-part of U.S. Pat. No. 7,869,563, filed Feb. 22, 2008, which is a national stage entry of PCT/US05/042613, filed Nov. 11, 2003, which claims priority to and the benefit of U.S. Provisional Application No. 60/631,296, filed Nov. 26, 2004. U.S. Pat. No. 8,565,372 is also a continuation-in-part and claims priority under 35 U.S.C. §120 to U.S. Pat. No. 7,831,296, filed Nov. 26, 2003, which is a continuation of U.S. Pat. No. 7,123,684, filed Nov. 27, 2002. Each of the above applications is hereby incorporated by reference.

FIELD OF THE INVENTION

This application relates to medical imaging and more specifically to a system and method of acquiring low-dose three-dimensional images and using the low dose images in combination with a conventional mammogram to enable improved detection of calcifications and masses with minimal patient dosing.

BACKGROUND

In the U.S. breast cancer mortality is second only to that of lung cancer. Because of its role in early tumor detection, mammography has come are the most commonly used tool for breast cancer screening, diagnosis and evaluation in the United States. A mammogram is an x-ray image of inner breast tissue that is used to visualize normal and abnormal structures within the breasts. Mammograms provide early cancer detection because they can often show a breast lumps and/or calcifications before they are manually palpable. problem with mammograms lies in their low specificity; that is it is often difficult to determine whether a detected abnormality is associated with a cancerous or benign lesion. The difficulty arises from the fact that a mammogram is two dimensional representations of a throe dimensional structure, and overlapping structures in the compressed breast may confound diagnosis.

Efforts to improve the sensitivity and specificity of breast x-rays have included the development of breast tomosynthesis systems. Breast tomosynthesis is a three-dimensional imaging technology that involves acquiring images of a stationary compressed breast at multiple angles during a short scan. The individual images are then reconstructed into a series of thin, high-resolution slices that can be displayed individually or in a dynamic ciné mode.

Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization. Examples of breast tomosynthesis systems are described in U.S. Pat. Nos. 7,245,694 and 7,123,684, commonly owned by the Assignee of this application.

One goal of any x-ray imaging system is to obtain the highest quality image while minimizing the patient dose. When selecting a radiation dose to use for imaging, a balance must be attained between image quality and patient safety. As a result an effort has been made to limit the dose of radiation administered during tomosynthesis imaging. For example, the article "Micro-Calcification Detection in Digital Tomosynthesis Mammography", by Wheeler et al. describes that a total patient dosing across tomosynthesis projection images in a single scan should be comparable to that administered during a two view mammography.

SUMMARY OF THE INVENTION

According to one aspect of the invention an improved breast imaging system and method reduces patient dose by leveraging the combined strengths of two-dimensional and three-dimensional imaging. The present invention recognizes that calcification detection should be performed by imaging at a radiation dose sufficient to reduce quantum mottle (essentially image noise caused by photon absorption) to a level which enables viewing of micro-calcifications. However, according to one aspect of the invention it is realized that the resolution needed to view calcifications is not required for viewing masses; rather the problem with accurate mass detection results from structure overlay. Thus three-dimensional imaging at a dose that is considerably less that that used for the 2-D imaging provides sufficient information for improved detection of masses. The combination of the 2D image and low-dose 3D image provides a breast cancer screening system with high sensitivity and specificity.

A tomosynthesis breast imaging system comprising an x-ray source and an x-ray detector, the x-ray source and x-ray detector configurable to acquire a two-dimensional image and a three-dimensional image, wherein the two-dimensional image is acquired at a first dose and the three-dimensional image is acquired at a second dose less than or equal to the first dose.

According to a further aspect of the invention an integrated mammography/tomosynthesis system includes an x-ray source and an x-ray detector, the x-ray source and x-ray detector configurable to acquire at least one of a mammogram and a set of tomosynthesis images, wherein the mammogram is acquired at a first dosage and the set of tomosynthesis images are acquired at a second dosage less than or equal to the first dosage.

According to another aspect of the invention, a method of imaging a breast including the step of acquiring a three-dimensional image of the breast using a lower dosage than used to acquire a two-dimensional image of the breast.

A method of imaging a breast including the steps of acquiring a low-dose three-dimensional image of the breast, acquiring a two-dimensional image of the breast using a dose corresponding to a mammogram imaging dose, using the conventional dose mammogram to locate calcifications in the breast and using the low-dose three-dimensional image to locate masses in the breast.

According to further aspect of the invention, a method of imaging a breast includes the steps of acquiring a two-dimensional image of a breast using a first x-ray dose, acquiring a three-dimensional image of the breast using a second x-ray dose less than the first x-ray dose and using the two-dimensional image and three-dimensional image to identify calcifications and masses in the breast.

In describing examples and preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

DETAILED DESCRIPTION

Figure 1:
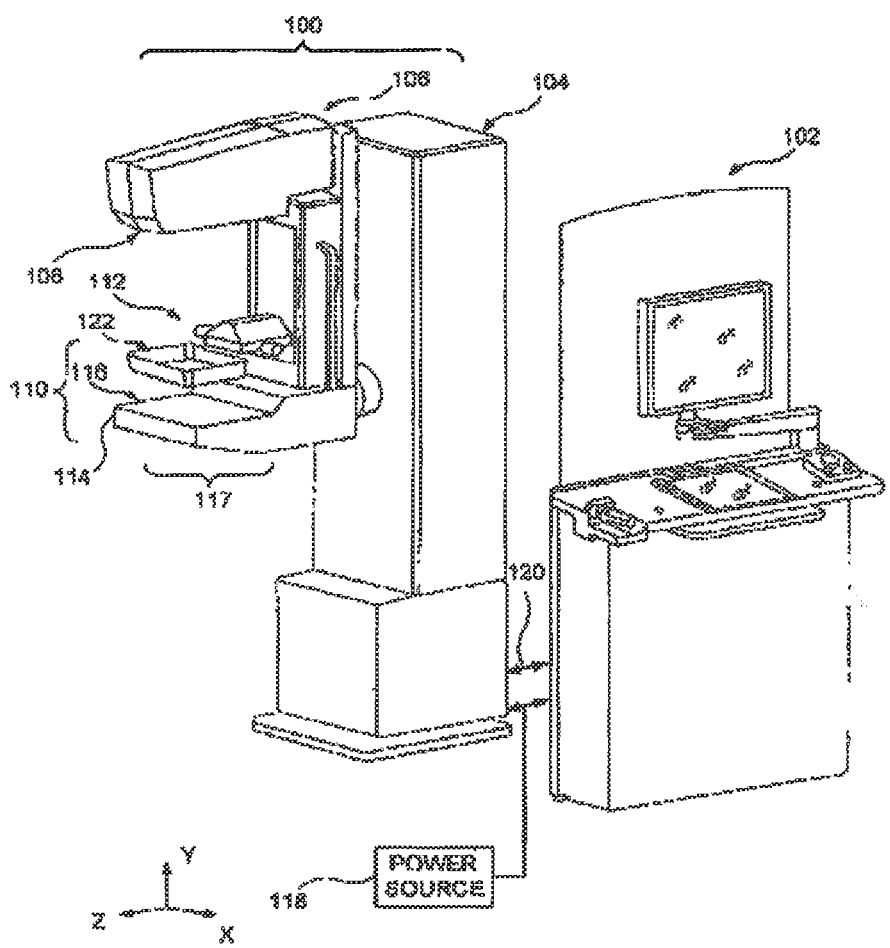
FIG. 1 is a perspective view of a gantry and an acquisition workstation in accordance with an example of the disclosed system.

Sensitivity is the ability of the imaging technology to detect a cancerous lesion. Specificity is the ability of the imaging technology to ignore artifacts in images which merely appear similar to lesions. The present invention leverages the combined strengths two-dimensional and three-dimensional imaging to provide a breast imaging system with improved sensitivity, specificity and the added advantage of reduced patient dosing.

One important characteristic of any digital imaging system is the ability to vary the amount and intensity of radiation used to generate any image. Radiation intensity is related to the atomic number (Z) of the x-ray target, the x-ray current (mA), x-ray voltage and x-ray beam filtration. Radiation intensity is varied to improve image quality, which in turn improves diagnostic sensitivity. When radiation intensity increases, quantum mottle (image noise caused by photon absorption) will decrease and visa versa.

Radiation intensity is directly related to patient dosage. The greater the intensity of radiation, the higher the x-ray dose to the patient. Much effort has been put into the design of mammography systems capable of acquiring a quality image at a lowest possible dosage. In the current full field digital mammography systems, the average mammogram dose is 1.2-1.5 mGy.

Many mammography and tomosynthesis systems allow the operator to control x-ray exposure by manually setting technique factors such as mA and mSec. Some systems include Automatic Exposure Control (AEC) functionality which control a duration of administration of radiation, turning off the x-ray source when the desired dose has been administered. Automatic Exposure Control (AEC) methods may vary the dosing parameters, including exposure time, kV, mA and filter modes for an image to vary the exposure and the radiation intensity. According to one aspect of the invention, AEC functionality of a tomosynthesis system may be used to reduce the dosage applied during a tomosynthesis scan, for example by changing any one of the above dosing parameters.

Alternatively (or in addition) the dosage may be controlled by limiting the angle of the scan and or the number of projection images obtained during a scan. The scan angle and number of projection images may also be controlled via a user interface located on the gantry or at the radiologists workstation.

In one embodiment, the sum of the dose administered during acquisition of all of the projection images (i.e., the tomosynthesis dose) is less than equal to the dose of a conventional mammogram. For example, the tomosynthesis dose may be in the range 0.25 to 1.0 of the dose used to acquire a single view of a conventional mammogram. In an exemplary embodiment it has been determined that sufficient information for calcification and mass detection may be obtained using a conventional mammogram view acquired with a dose of 1.0-1.5 mGy and three-dimensional image reconstructed from fifteen projection images taken at a total dose of 0.6 mGy. In an alternate embodiment, the total dose of 0.6 mGy may be administered from projection images obtained by performing an angular scan over 7°, and obtaining, for example, 7 projection images. Such an arrangement allows the three-dimensional data to be obtained at a lower dose and faster scan time. An additional advantage of low-dose tomosynthesis acquisition is that it increases the longevity f the x-ray tube.

FIGS. 1-6 illustrate a non-limiting example of a multi-mode mammography/tomosynthesis system embodying the present invention. The system comprises a gantry 100 and a data acquisition work-station 102. Gantry 100 includes a housing 104 supporting a tube arm assembly 106 rotatably mounted thereon to pivot about a horizontal axis 402 (FIG. 4) and carrying an x-ray tube assembly 108. A spacer 1002 can be used for magnification. If x-ray receptor 502 remains in place despite rotation of arm 106, or if spacer 1002 is used, anti-scatter grid 504 is fully retracted; if x-ray receptor 502 maintains its orientation relative to tube arm assembly 106 and no spacer 1002 is used, anti-scatter grid 504 need not be retracted. As is known in the art, the two or more images can be used to identify the location of a lesion, so that needle biopsy can be used, for example with an upright needle biopsy station 412 (FIG. 4) in a manner similar to that used with the commercially available Selenia™ system and StereoLoc II™. A compression paddle 122 appropriate for needle biopsy typically is used when taking the stereotactic images. Alternatively, some or all of the images taken in the tomosynthesis mode and/or in the combined mode can be used to identify the location of a lesion for biopsy, in which case a compression paddle 122 appropriate for the purpose typically is used when taking the images. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple filters such as molybdenum, rhodium, aluminum, copper, and tin filters, and (3) an adjustable collimation assembly selectively collimating the x-ray beam from the focal spot in a range such as from 7×8 cm to 24×29 when measured at the image plane of an x-ray image receptor included in the system, at a maximum source-image distance such as 75 cm. Also mounted on housing 104, for rotation about the same axis 402, is a compression arm assembly 110 that comprises a compression plate 122 and a receptor housing 114 having an upper surface 116 serving as a breast plate and enclosing a detector subsystem system 117 comprising a flat panel x-ray receptor 502 (FIG. 5), a retractable anti-scatter grid 504 and a mechanism 506 for driving and retracting anti-scatter grid 504. Two knobs 510d, one on each lateral side of support 510, can be manually rotated to move projection 510b and thus compression paddle 122 laterally such that it compresses a breast that is not centered laterally on upper surface 116, for example for MLO imaging. Each knob 510d can operate a mechanism such as an endless screw rotating in a nut secured to projection 510b. Alternatively, or in addition, projection 510b and thus compression paddle 122 can be driven laterally by a motor, under control of operator switches or other interface at gantry 100 or at work-station 102, or automatically positioned laterally under computer control. Housing 104 also encloses the following components schematically illustrated in FIG. 4: a vertical travel assembly 404 for moving tube arm assembly 106 and compression arm assembly 110 up and down to accommodate a particular patient or imaging position, a tube arm assembly rotation mechanism 406 to rotate tube arm assembly 106 about axis 402 for different imaging positions, a detector subsystem rotation mechanism 408 for rotating components of detector subsystem 117 (such as x-ray receptor 502) about axis 402 to accommodate different operations modes, and couple/uncouple mechanism 410 to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here. A patient shield 200, schematically illustrated in FIG. 2, can be secured to compression arm assembly 110 to provide a mechanical interlock against patient contact with the rotating x-ray tube arm assembly 106. Work-station 102 comprises components similar to those in the Selenia™ mammography system, including a display screen (typically a flat panel display that may include touch-screen functionality), user interface devices such as a keyboard, possibly a touch-screen, and a mouse or trackball, and various switches and indicator lights and/or displays. Work-station 102 also includes computer facilities similar to those of the Selenia™ system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers workstation 102. Gantry 100 and work-station 102 exchange data and controls over a schematically illustrated connection 120.

Figure 6:
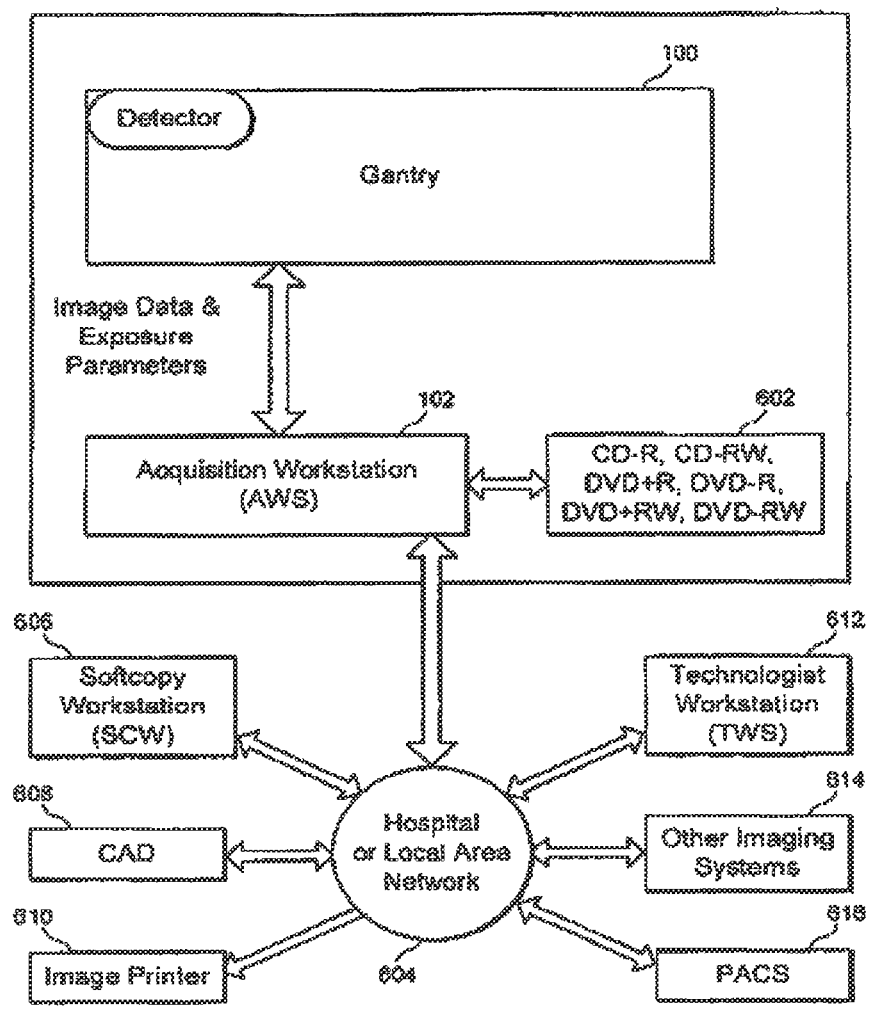
FIG. 6 is a block diagram of the disclosed system when connected to other systems.

As illustrated in FIG. 6, additional storage facilities 602 can be connected to work-station 102, such as one or more optical disc drives for storing information such as images and/or for providing information to work-station 102 such as previously obtained images and software, or a local printer (not shown). In addition, the disclosed system can be connected to a hospital or local area or other network 604, and through the network to other systems such as a soft copy workstation 606, a CAD (Computer Aided Detection) station 608 for computer-processing mammography and/or tomosynthesis images to identify likely abnormalities, an image printer 610 for printing images, a technologist workstation 612, other imaging systems 614 such as other mammography systems or systems for other modalities for exchange of images and/or other information, and to a PACS (Picture Archiving) systems 616 for archiving images and other information and/or retrieving images and other information.

In standard mammography mode, typically used for screening mammography, tube arm assembly 106 and compression arm assembly 110 are coupled and locked together by 410 in a relative position such as seen in FIG. 1, such that an x-ray beam from x-ray tube assembly 108 illuminates x-ray receptor 502 when the patient's breast is compressed by compression device 112. In this mode, the system operates in a manner similar to said Selenia™ system to take a mammogram. Vertical travel assembly 404 and tube arm rotation mechanism 406 can make vertical adjustments to accommodate a patient, and can rotate tube arm assembly 106 and compression arm assembly 110 together as a unit about axis 402 for different image orientations such as for CC and for MLO images. For example, tube arm assembly 106 and compression arm assembly 110 can rotate between (−195.degree.) and (+150.degree.) about axis 402. As in the Selenia™ system, compression device 112 includes a compression paddle 122 that can move laterally, in a direction along the chest wall of a patient, to adjust for different imaging orientations. However, as described further below, the mechanism for supporting and moving compression paddle 122 is different. Typically, anti-scatter grid 504 is over x-ray receptor 502 in the standard mammography mode to reduce the effect of x-ray scatter.

Figure 2:
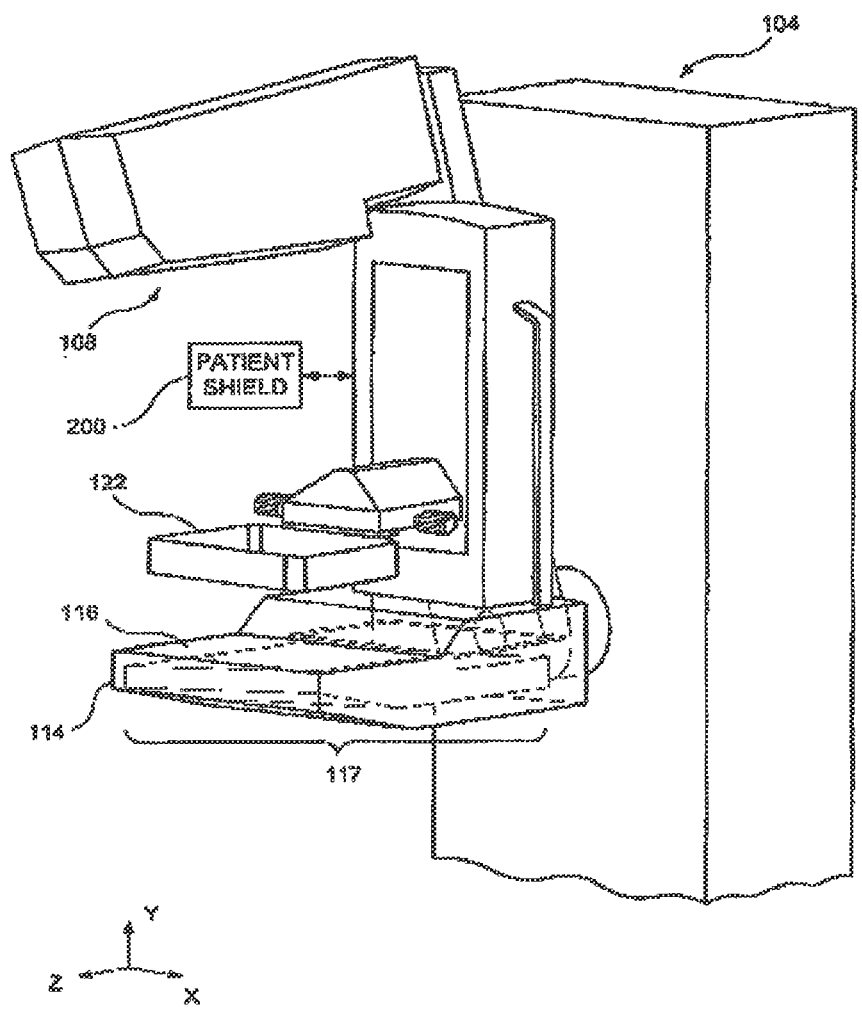
FIG. 2 is an enlarged view of a portion of the system of FIG. 1, with a tube arm assembly in a rotated position.

In tomosynthesis mode, tube arm assembly 106 and compression arm assembly 110 are decoupled by unit 410 such that compression arm assembly 110 stays in one position, compressing the patient's breast, while tube arm assembly 106 rotates about axis 402, for example between the position illustrated in FIG. 2 to that illustrated in FIG. 11, or .+−.15.degree. relative to compression arm assembly 110. Tomosynthesis can be carried out for different image orientations, so that compression arm assembly 110 can be rotated about axis 402 (alone or together with assembly 106) for a desired image orientation and locked in place, and then tube arm assembly 106 can be rotated relative to that position of compression arm assembly 110 for tomosynthesis imaging over .+−.15.degree. or some other desired angular range. For example, low dose tomosynthesis may be performed over a seven degree angular range to collect in the area of seven projection images.

Figure 3:
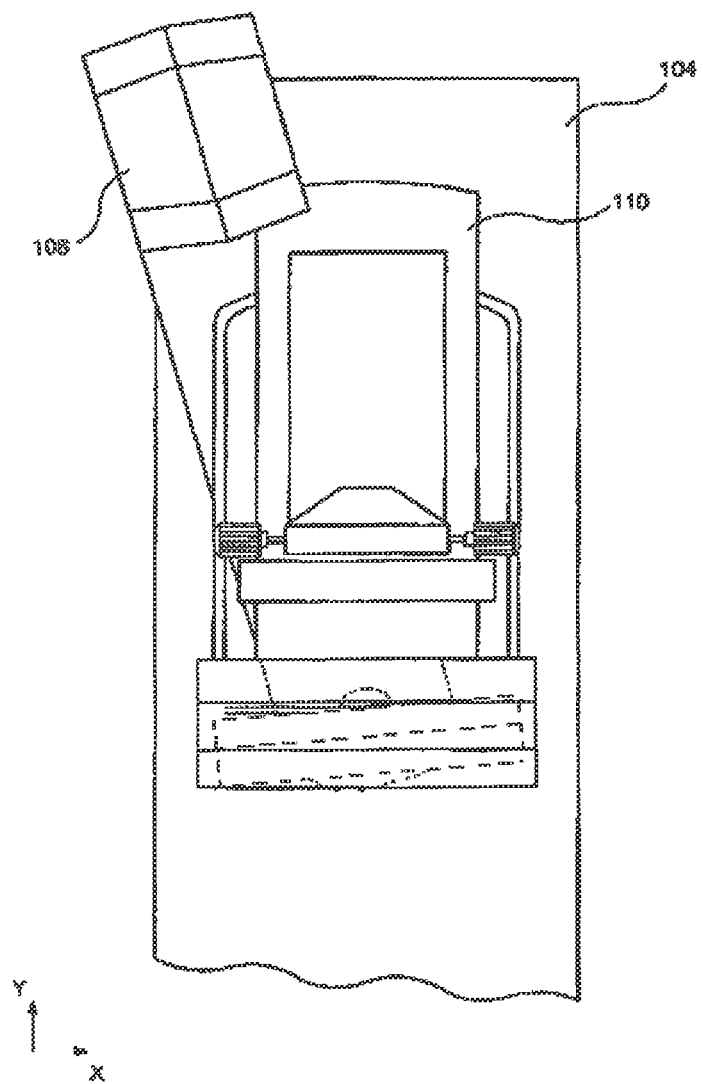
FIG. 3 is a front elevation of the apparatus of FIG. 2.
Figure 4:
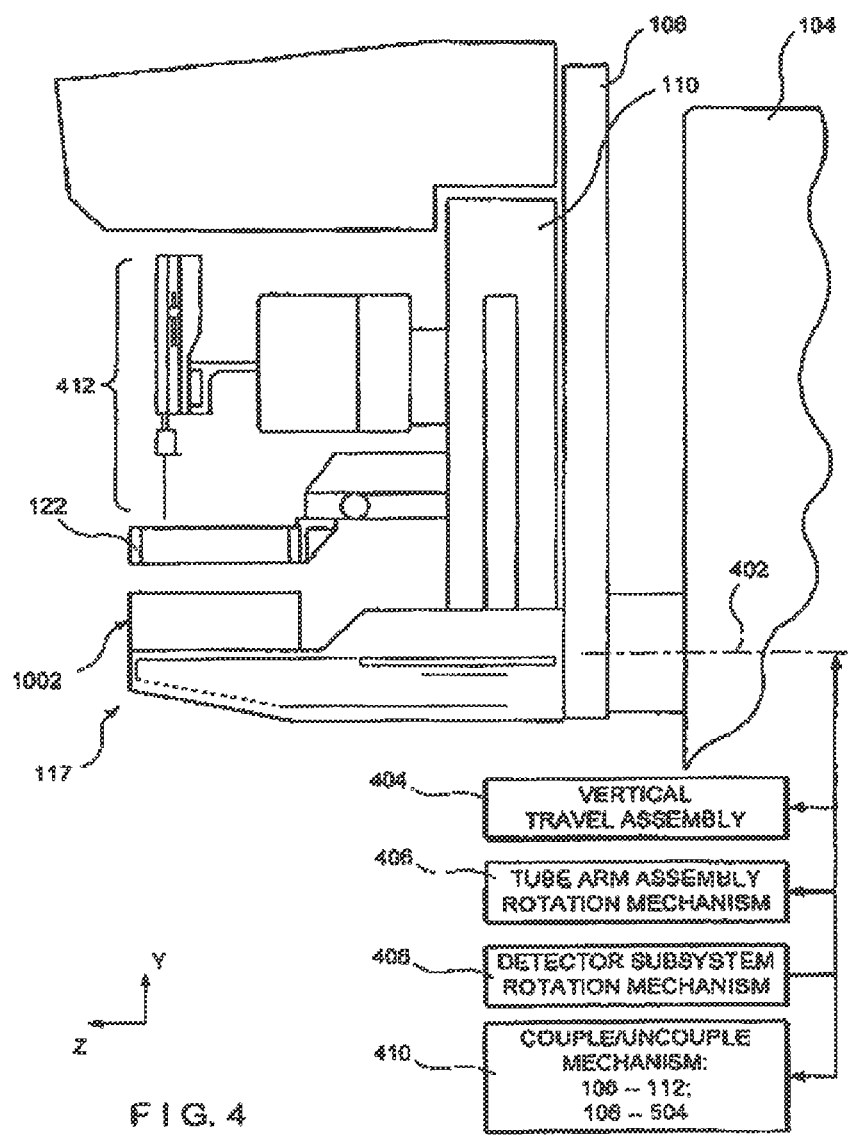
FIG. 4 is a side view of a gantry with a biopsy station and a spacer, with schematic illustration of other mechanisms.
Figure 5:
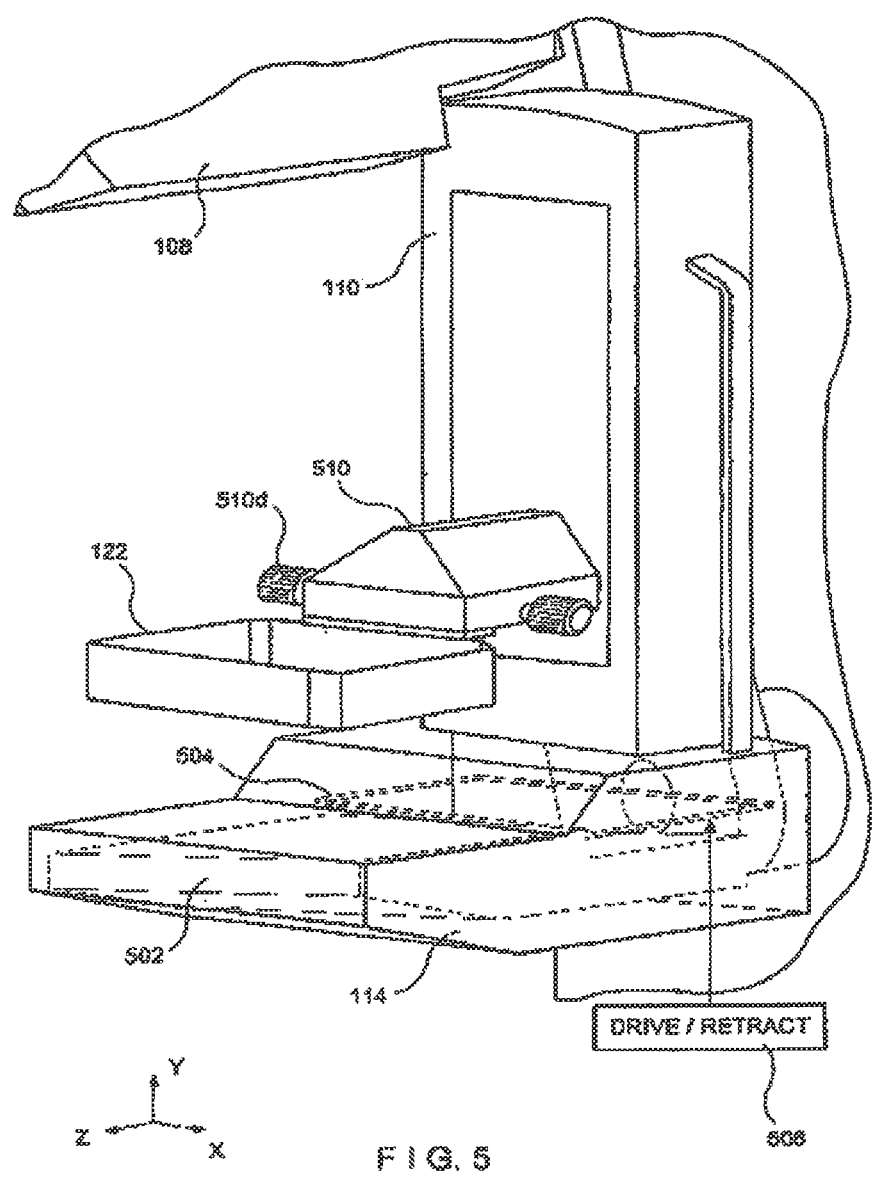
FIG. 5 is an enlarged view of a portion of FIG. 1.

In one example, 11 images are taken during an angular sweep of tube arm assembly 106, one every approximately 3.degrees. However, a different number of images can be taken, for example up to 21 during a single sweep. For tomosynthesis images, the x-ray tube in x-ray tube assembly 108 continuously rotates and the x-ray tube is pulsed for each image, for example, for x-ray energy pulses each lasting approximately 100 mSec, although pulses of different duration can be selected. Alternatively, the rotational motion can stop for taking each image, or continuous motion without pulsing can be used (and the timing of data measurements relied to define pixel values). As seen in FIGS. 2, 3 and 5, in this mode mechanism 506 fully retracts anti-scatter grid 504 away from x-ray receptor 502 so grid 504 is out of the image. Also as seen in these Figs., while the breast remains immobilized in compression arm assembly 110 during the angular sweep of tube arm assembly 106, x-ray receptor 502 rocks within receptor housing 114. In this rocking motion, controlled by unit 408 (FIG. 4), a line normal to the image face of x-ray receptor 502 may keep pointing to the focal spot of the x-ray tube in x-ray tube assembly 108. Alternatively, the rotation of tube arm assembly 106 and rocking of x-ray receptor 502 can be through different angles; for example, tube arm assembly 106 can rotate through 15.degree. while x-ray receptor 502 rocks through 5.degree., i.e. the rocking angle can be an amount one-third that of assembly 108. Synchronous rotation of tube arm assembly 106 and rocking of x-ray receptor 502 can be achieved by controlling separate motors for each or, alternatively, through using a motor to drive tube arm assembly 106 and a mechanical coupling between the rotation of tube arm assembly 106 and rocking of x-ray receptor 502.

Image data can be obtained and processed into tomosynthesis images for display and/or storage as described in the material incorporated by reference, for example in copending patent application Ser. No. 10/723,486 or in U.S. Provisional Application No. 60/628,516, filed Nov. 15, 2004.

In a combination mode, during a single compression of the patient's breast the system takes a conventional mammogram and tomosynthesis images. In this mode, while the breast remains compressed in compression arm assembly 110, (1) tube arm assembly 106 sweeps and x-ray receptor 502 rocks, each through an appropriate angle, and exposures are taken for tomosynthesis images, and (2) a standard mammogram is taken. The standard mammogram can be taken at a 0.degree. relative angle between tube arm assembly 106 and a normal to the imaging plane of x-ray receptor 502, and can be taken before or after the tomosynthesis images are taken or between the taking of two successive tomosynthesis images. Typically, each tomosynthesis image utilizes substantially lower x-ray dose than the standard mammogram.

For example, as described above, the total dosage of all projection images taken during the tomosynthesis scan can range from 0.25 to 1.0 times that of a single dose of a mammogram. The relationship between the two dosages can be user-selected to control any one of the x-ray tube voltage, current, tomosynthesis scan angle, number of projection images obtained, etc. In alternate embodiments, the dosage may be altered via a simple switch on the gantry, or view a user control at a radiologist workstation. In still alternate embodiments the dosage may vary automatically as the radiologist switches between modes.

Figure 7:
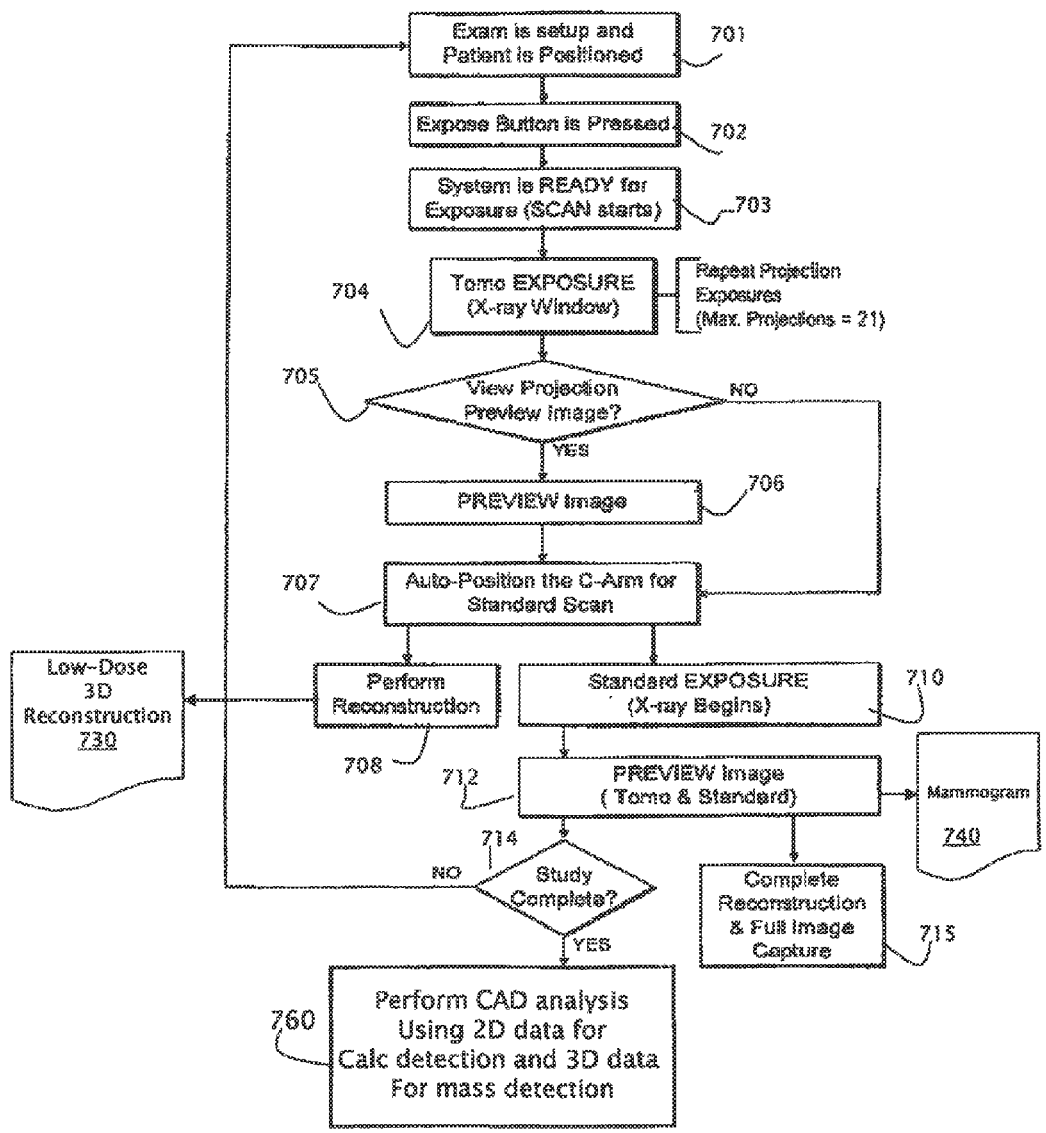
FIG. 7 is a flow chart illustrating one of several examples of work flow for a combination mode.

FIG. 7 illustrates an example of workflow for performing mammography and tomosynthesis in a combination mode. At step 701 the system is set for a tomosynthesis scan, and the required dosage is either input manually or updated automatically in response to a selected mode of operation. During steps 702-708 the low dose tomosynthesis image 730 is acquired. During steps 710-715 the mammogram 740 is acquired. At step 760, CAD is performed using the 2D image for calc detection and the 3D image for mass detection.

Again, these are examples, and different steps or orders of steps can be used instead. For example, a preferred approach may be to take the standard mammogram first, then move arm 106 to one end of its rotational range for tomosynthesis and take the tomosynthesis images. The order in which the two types of images are taken may be optimized such that the overall imaging time is minimized, and an order that achieves such minimization can be the preferred order. The exposure (tube current mA, tube voltage kVp, and exposure length msec) techniques for the standard mammogram and the tomosynthesis exposures can be set manually, or by using automatic methods. If the standard mammogram is taken first, its exposure techniques can be used to set an optimal technique for the subsequent tomosynthesis images, and vice versa. The exposure technique can be modified dynamically, if the software senses that the signal reaching the image receptor is either too low or too high and adjust subsequent exposures as needed.

Although the above has described the use of the present invention with regard to a system which supports acquisition of both tomosynthesis and mammogram images, the present invention is not limited to an integrated multi-mode system but may also be used in any system that is capable of performing tomosynthesis. For example the present invention may be used in a system which includes only tomosynthesis imaging capability. Such systems may use a legacy mammogram for example for calcification detection, or may obtain a single tomosynthesis image at higher dosage to use as their 2D image. In addition, the present invention may be used in any system which incorporates tomosynthesis imaging capability with a different modality, such as molecular breast imaging or ultrasound imaging. In short any breast imaging systems which includes tomosynthesis imaging capabilities falls within the scope of the present invention.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A method of imaging a breast using a multi-mode mammography/tomosynthesis system, the method comprising:
acquiring a two-dimensional image of a breast using a first x-ray dose in a first mode of operation of the multi-mode mammography/tomosynthesis system, wherein the first x-ray dose is emitted from an emission source when the emission source is stationary; and
acquiring a set of tomosynthesis images of the breast in a second mode of operation of the multi-mode mammography/tomosynthesis system, wherein the set of tomosynthesis images is acquired from a plurality of projection images, wherein each of the plurality of projection images is acquired at a projection image x-ray dose less than the first x-ray dose, wherein each projection image x-ray dose is emitted when the emission source is rotating relative to the breast.

2. The method of claim 1, wherein the two-dimensional image is acquired at an angle similar to that of a conventional mammogram.

3. The method of claim 1, wherein the two-dimensional image is used to identify calcifications in the breast and the set of tomosynthesis images is used to identify masses in the breast.

4. The method of claim 3, wherein identification of calcifications in the breast is accomplished via a CAD mark representative of the calcification on the two-dimensional image.

5. The method of claim 3, wherein identification of masses in the breast is accomplished via a CAD mark representative of the masses on the set of tomosynthesis images.

6. The method of claim 1 further comprising controlling the projection image x-ray dose administered for acquisition of the set of tomosynthesis images, the controlling the projection image x-ray dose comprising adjusting at least one of an x-ray tube voltage, x-ray current, x-ray filter, exposure time, and combinations thereof.

7. The method of claim 1 further comprising controlling the projection image x-ray dose administered for acquisition of the set of tomosynthesis images, the controlling the projection image x-ray dose comprising adjusting at least one of a tomosynthesis scan angle and a number of projection images obtained for the set.

8. The method of claim 1 further comprising using an anti-scatter grid for the first mode of operation of the multi-mode mammography/tomosynthesis system.

9. The method of claim 1, wherein the projection image x-ray dose is updated automatically in response to selection or use of the second mode of operation.

10. The method of claim 1, wherein a total x-ray dosage of the plurality of projection images is input manually.

11. The method of claim 1, wherein a total dosage of the plurality of projection images x-ray doses is less than the first x-ray dose.

12. A multi-mode mammography/tomosynthesis system comprising:
   an x-ray source configured to move along an arc; and
   an x-ray detector;
   wherein the x-ray source and the x-ray detector are configured to (a) acquire a two-dimensional image of a breast using a first x-ray dose in a first mode of operation, wherein the two-dimensional image is acquired when the x-ray source is stationary and (b) acquire a set of tomosynthesis images of the breast in a second mode of operation, wherein the set of tomosynthesis images is acquired with a plurality of projection images, wherein each of the plurality of projection images is acquired at a projection image x-ray dose less than the first x-ray dose, and wherein the plurality of projection images are acquired when the x-ray source is moving along the arc.

13. The system of claim 12, wherein the two-dimensional image is acquired at an angle similar to that of a conventional mammogram.

14. The method of claim 12, wherein a total dosage of the plurality of projection images x-ray doses is less than the first x-ray dose.

15. A method of imaging a breast using a multi-mode mammography/tomosynthesis system, the method comprising:
   acquiring a two-dimensional image of a breast using a first x-ray dose in a first mode of operation of the multi-mode mammography/tomosynthesis system, wherein the first x-ray dose is emitted from a stationary position; and
   acquiring a set of projection images of the breast in a second mode of operation of the multi-mode mammography/tomosynthesis system, wherein each image of the set of projection images is acquired at a second x-ray dose less than the first x-ray dose, wherein the second x-ray dose is emitted during a rotational movement of an x-ray source that emits the x-ray.

16. The method of claim 15, wherein the two-dimensional image is acquired at an angle similar to that of a conventional mammogram.

17. The method of claim 15 further comprising controlling the second x-ray dose administered for acquisition of the set of tomosynthesis images, the controlling the second x-ray dose comprising adjusting at least one of an x-ray tube voltage, x-ray current, x-ray filter, exposure time, and combinations thereof.

18. The method of claim 15 further comprising controlling the second x-ray dose administered for acquisition of the set of tomosynthesis images, the controlling the second x-ray dose comprising adjusting at least one of a tomosynthesis scan angle and a number of projection images obtained for the set.

19. The method of claim 15, wherein the second x-ray dose is updated automatically in response to selection or use of the second mode of operation.

20. The method of claim 15, wherein a total dosage of the set of projection images is less than the first x-ray dose.

* * * * *